United States Patent
Ren et al.

(10) Patent No.: US 11,963,751 B2
(45) Date of Patent: *Apr. 23, 2024

(54) HUMAN BIOELECTRICAL SIGNAL DETECTION AND MONITORING

(71) Applicant: LR Technologies, Inc., Rockville, MD (US)

(72) Inventors: Eugene Yu-Jiun Ren, San Marcos, CA (US); Yexian Qin, Tuscon, AZ (US); Chiehping Lai, Rockville, MD (US)

(73) Assignee: LR TECHNOLOGIES, INC., Rockville, ND (US)

( * ) Notice: Subject to any disclaimer, the term of this patent is extended or adjusted under 35 U.S.C. 154(b) by 793 days.

This patent is subject to a terminal disclaimer.

(21) Appl. No.: 17/090,259

(22) Filed: Nov. 5, 2020

(65) Prior Publication Data
US 2021/0275050 A1 Sep. 9, 2021

Related U.S. Application Data

(63) Continuation-in-part of application No. 16/277,968, filed on Feb. 15, 2019, now Pat. No. 10,856,765.
(Continued)

(51) Int. Cl.
*A61B 5/05* (2021.01)
*A61B 5/00* (2006.01)
(Continued)

(52) U.S. Cl.
CPC .................. *A61B 5/05* (2013.01); *A61B 5/25* (2021.01); *A61B 5/363* (2021.01); *A61B 5/369* (2021.01);
(Continued)

(58) Field of Classification Search
CPC ....... A61B 5/05; A61B 5/7264; A61B 5/0476; A61B 5/6804; A61B 5/721; A61B 5/0464; H04Q 9/02; H04Q 2209/40; H01Q 1/273
See application file for complete search history.

(56) References Cited

U.S. PATENT DOCUMENTS 10,206,602 B2 * 2/2019 Ren ...................... A61B 5/6804
10,856,765 B2 * 12/2020 Ren ........................ H01Q 1/273

OTHER PUBLICATIONS

Sullivan, Thomas J., et al., "A Low-Noise, Non-Contact EEG/ECG Sensor", IEEE Biomedical Circuits and Systems Conference 2007, Montreal, Quebec, Canada, Nov. 27-30, 2007, pp. 154-157.

* cited by examiner

*Primary Examiner* — Rex R Holmes
(74) *Attorney, Agent, or Firm* — Perkins Coie LLP

(57) ABSTRACT

The present disclosure includes an electromagnetic field detection and monitoring system. The system includes a single-ended amplifier and an impedance matching circuit which matches the impedance caused by an air gap between tissue and an electrode. The system includes passive detection, active detection, and signal processing capabilities. At least one embodiment includes a body worn system with sensing, processing, communications, and data storage capabilities. The system provides wearable antennas to transfer the EMF energy in its electrical or magnetic forms into the sensor efficiently. A specially designed processing algorithm can process the collected data and generated the results for medical professionals to read and make decisions. The processing can include machine learning technique which decompose an EMF signal into EEG bands to perform feature extraction. The features can then be used to train a machine learning model to classify other EMF signals.

31 Claims, 13 Drawing Sheets

Related U.S. Application Data which is a continuation of application No. 15/946,715, filed on Apr. 5, 2018, now Pat. No. 10,206,602.

(60) Provisional application No. 62/482,123, filed on Apr. 5, 2017.

(51) Int. Cl.
| | |
|---|---|
| *A61B 5/25* | (2021.01) |
| *A61B 5/363* | (2021.01) |
| *A61B 5/369* | (2021.01) |
| *H01Q 1/22* | (2006.01) |
| *H01Q 1/27* | (2006.01) |
| *H01Q 1/48* | (2006.01) |
| *H01Q 5/335* | (2015.01) |
| *H01Q 21/28* | (2006.01) |
| *H04Q 9/00* | (2006.01) |
| *H04Q 9/02* | (2006.01) |

(52) U.S. Cl.
CPC ............ *A61B 5/6804* (2013.01); *A61B 5/721* (2013.01); *A61B 5/7264* (2013.01); *H01Q 1/2291* (2013.01); *H01Q 1/273* (2013.01); *H01Q 1/48* (2013.01); *H01Q 5/335* (2015.01); *H01Q 21/28* (2013.01); *H04Q 9/00* (2013.01); *H04Q 9/02* (2013.01); *H04Q 2209/40* (2013.01)

HUMAN BIOELECTRICAL SIGNAL DETECTION AND MONITORING

CROSS REFERENCE TO RELATED APPLICATIONS

This application is a continuation in part of U.S. patent application Ser. No. 16/277,968 filed on Feb. 15, 2019, now issued as U.S. Pat. No. 10,856,765, which is a continuation of U.S. patent application Ser. No. 15/946,715, filed Apr. 5, 2018, now issued as U.S. Pat. No. 10,206,602, issued on Feb. 15, 2019, which claims priority to U.S. Provisional Patent Application Ser. No. 62/482,123, filed on Apr. 5, 2017, the entire contents of which are hereby incorporated by reference.

GOVERNMENT LICENSE RIGHTS

Some embodiments of the invention were made with government support under W81XWH-17-C-0133 awarded by the U.S. Army Medical Research and Materiel Command. The government has certain rights in the invention.

TECHNICAL FIELD

The present disclosure is directed generally to electromagnetic field detection and monitoring system, and more specifically, to monitor a soldier or field operator's health condition based on electromagnetics field (EMF) signals emitted from the human body.

BACKGROUND

In a dynamic, fast changing environment, and especially a hostile one such as a warzone, it is preferable to be able to accurately, timely, and reliably monitor the health condition of a field operator.

The EMF signals from the human body are emitted at two extreme ends of the electromagnetic spectrum. The two extremes correspond to very low (e.g., KHz to Hz range) and very high (e.g., equal or higher than THz) frequencies on the electromagnetic spectrum. In order to detect bioelectrical signals from the human body, infrared radiation (e.g., THz range) may be projected on, and electrodes attached to, the skin for obtaining electroencephalogram (EEG) or electrocardiography (ECG) signals.

There are technical difficulties in implementing a health monitoring system that is based on monitoring these electromagnetic signals of two extreme ends and nevertheless suitable for said dynamic, fast changing environment.

DETAILED DESCRIPTION

Figure 1:
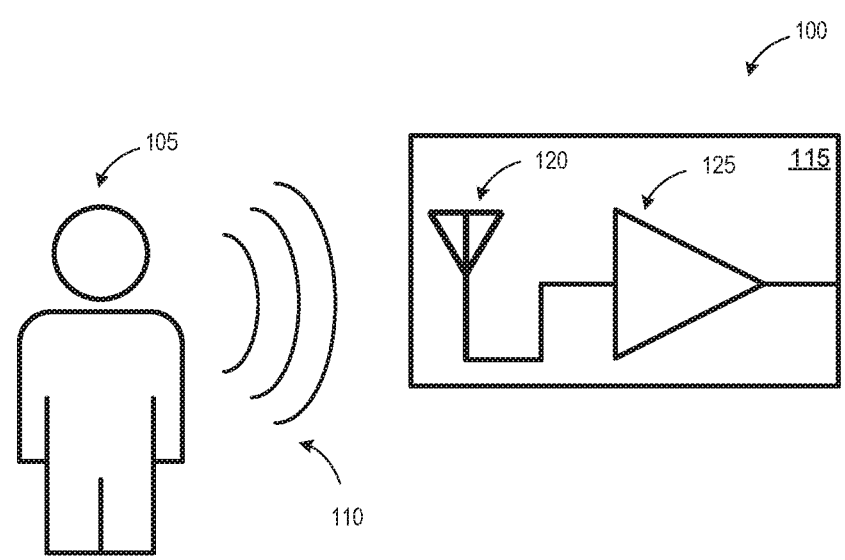
FIG. 1 is a diagram of a passive detection environment in accordance with one or more embodiments of the present disclosure.

In order to achieve the goal of detecting the physical conditions of a human body in a fast changing and dynamic environment, such as a warzone, there are a number of technical hurdles. First, the wearable antennas should be thin, lightweight, low maintenance, robust, inexpensive and easily integrated in sensing circuits. Second, the system should be able to detect a frequency range between the extremely low frequency (ELF) band to the very low frequency (VLF) band. ELF is defined by the International Telecommunication Union (ITU) as electromagnetic radio waves with frequencies from 3 to 30 Hz. VLF is defined by the International Telecommunication Union (ITU) as electromagnetic radio waves with frequencies from 3 kHz to 30 kHz. Third, system must be able to exclude uncertainty from weak EMF signals. Fourth, the detected EMF signals must be processed to obtain bioelectrical signals that are useful for health monitoring and medical diagnostics. Fifth, a detection system can match impedances caused by a prior stage. In particular, the impedance caused by an air gap between tissue and the corresponding electrode can fluctuate based on the movement of the subject. Last but not least, the detection system needs to be non-intrusive so as not to adversely affect the subject's performance, and yet maintains an acceptable level of accuracy. There are additional challenges for the selection of textile materials, circuit assembly, manufacturing, and performance reliability.

Traditional EMF signal detection utilizes contact-based electrodes. The electrode can be a tiny patch that connects to the patient for sensing bioelectric potential. This electrical activity can be viewed as a small electric field or flux of charge-carrying particles (i.e., current). The electrodes work as transducers that convert the current flow from the body into the electron flow of the metallic wire. Often a high ionic concentration gel is used in the skin-electrode interface to increase conductivity due to small signal magnitude.

However, such an implementation faces several disadvantages. For example, one disadvantage is the time and effort necessary to create an initial contact between the electrode and the skin. Another disadvantage is that the connection between the electrode and the skin may deteriorate over time. This may occur when the high ionic concentration gel dries over time. This may also occur if the electrode is pulled away from the skin. When the contact deteriorates, the quality of the signal falls drastically. This concern is especially important in a fast changing and dynamic environment, such as a warzone where the electrode's contact to the patient's skin deteriorates rapidly. Additionally, the electrode may impede movement of the subject resulting in undesirable and dangerous loss of performance in the environment.

There have been implementations that attempt contactless EMF detection by using traditional electrodes and operates by capacitive coupling. In other words, the electrode that operates by capacitive coupling treats the gap between the electrode and the skin as a large capacitor. Such a model has the drawback that the coupling capacitance decreases rapidly as the distance between the electrode and the skin increases. Therefore, the electrode may only operate in a limited distance from the skin. Also, it is difficult to discern the locations of the signal sources in such implementation. These limitations make this model not suitable for EMF detection in a fast changing and dynamic environment.

Traditionally, only contact-based electrodes have been used for bioelectrical signal detection because there are several challenges to non-contact EMF detection. Antenna-based EEG/ECG signal detection occurs at a distance from the skin that is greater than the distance between a contact-based electrode and the skin. The antenna frequency is very low (10 Hz to 10 KHz) and thus its wavelength is long (e.g., the wavelength of a 5 KHz signal is about 60,000 meters and the wavelength of a 10 Hz signal is about 30,000,000 meters). Additionally, the minimum required electrical wavelength for the traditional antenna is 0.1 wavelength to guarantee an efficient radiation efficiency. Therefore, antenna-based EEG/ECG has not been implemented because the large size of the antenna would be cumbersome and dangerous in a fast changing and dynamic environment.

Accordingly, introduced here is a technique to measure and track EMF signals (e.g., 0 kHz to 30 kHZ), which is based on a new concept of detecting both contact and non-contact EMF signals. Additionally, signal processing can be performed by one or more embodiments for signature extraction and for rejecting interference from EMF signals. More specifically, the embodiments disclosed here can use a single or multiple EMF sensors that can be placed at various strategic locations, where the locations can enable the sensors to detect valuable signs of trauma and forecast physical conditions impacting the human's ability to operate missions in the field or during training process. The placement of such sensors can be part of an electro-textile combat and operations uniform. Some embodiments provide a body worn system equipped with sensing, processing, communications, and storage capabilities. The concept of the disclosed sensing system is to have wearable antennas capable of transferring the EMF energy in its electrical or magnetic forms into the sensors. The EMF energy is then processed to obtain bioelectrical signals indicating the physical conditions of the monitored human body.

EMF can be acquired from self-emission (i.e., passive detection) and reflection (i.e., active detection) from the human body. EMF self-emission is a function of numerous components. For example, random or pseudo noise can be induced by human muscle activities, minor currents near brain or heart, and body static excitations. Electromagnetic (EM) reflection is induced by the incoming EM energy from an external EM source coupling to the human body then the re-emission is excited. Both self and reflected EMF can be measured using electrical probes, magnetic loops, and antenna systems with good receiver sensitivity at the low end of the EM spectrum. Between two extremes of EM spectrum, these signals are usually very weak due to no-higher-frequency human energy emission (e.g., muscle pulse). Additionally, most of the non-linear effects in higher frequency are happening very short in time and narrow in its dynamic range in terms of amplitude.

Passive measurements may play a critical role in defining the state of the biological system. Active measurements on dead systems or selected organic chemical solutions along with passive intermodulation measurements and signal processing is used to further define the biological system in detail. ECG/EEG signals vary from the microvolt to the millivolt range and are the relatively stronger signal in human tissue. Due to this small voltage, the signals measured need to be amplified for better access.

In accordance with some embodiments, biopotential amplifiers may have high input impedance and are designed for safety, since excessive induced current may produce a significant shock to the living organism. Isolation and protection circuitry limit the any currents through the electrodes to safe levels. For proper interface to outside circuits, the output impedance of the amplifier desirably should be very low, allowing to drive any external loads with a minimal distortion. The amplifiers desirably should have a high rejection ratio (e.g., in differential mode) to eliminate large offset signals. Generally speaking, a rejection ratio of 30 db (i.e., 1000 times) may be considered "high." One of the most factors of EMF detection is the noise level, or noise floor, which is highest at lower frequencies. Therefore, according to one or more embodiments, biopotential amplifiers are differential which can minimize noise from the ground.

Further, in some embodiments, the EMF detection system can perform active harmonic signal calibration in order to understand and calibrate the intermodulation from the mixer, cables, signal generators, and digitizer. In particular, the system can perform a two-tone measurement around the frequency range of the interested signals and, in some implementations, up to the 7th order of its harmonics. For example, the test starts with two-tone signals feeding into the RF mixer in its working frequency range. The frequency mixer may have a low-frequency local oscillator (LO) signal, which may be as low as 500 Hz, in some examples. The system can also feed two tones above 500 Hz and can, for example, sweep the LO with a 100-Hz step frequency from 5 kHz to 5.5 kHz and keep the input signal at 1000 Hz.

The EMF detection system can also perform vital signal generation by waveform generator and active measurement. In some examples, the system generates a body signal (e.g., an ECG signal) and then measures the detected signal. In order to differentiate a normal ECG signal and arrhythmias signal, the system generates three different ECGs. One is a normal ECG signal, and the other two are arrhythmias (e.g., tachycardia and bradycardia). Each signal contains different features in both the time and frequency domain (e.g., such as the bandwidth changes). For example, tachycardia has a wider bandwidth than the normal ECG, and bradycardia has a narrower bandwidth than the normal one.

Finally, the EMF detection system can perform ECG signal detection at different locations of the body. At each measurement point, ECG may be recorded for 10 seconds at the sampling rate of 1000 samples/second. A low pass filter is applied to clean the signal. Both the original ECG signal and filtered signal may be plotted together for comparison. Additionally, the FFT spectrum of each original ECG signal may be used to analyze the results. Depending on the implementation, the system can also measure vital signals measured at different body positions. It is observed that ECG signal typically still dominates the vital signal detection, but other types of vital signal from the frequency domain, such as a 20 Hz signal around the stomach. This 20 Hz vital signal may be generated from stomach or intestine activities.

As described in further detail below, the disclosed embodiments here can further include a hybrid sensor system and signal processing to capture the EMF effects and track the EMF signatures in time and time-frequency domains. Notably, the disclosed system design makes the EMF tractable and repeatable.

In the following, numerous specific details are set forth to provide a thorough understanding of the presently disclosed technology. In other embodiments, the techniques introduced here can be practiced without these specific details. In other instances, well-known features, such as specific fabrication techniques, are not described in detail in order to avoid unnecessarily obscuring the present disclosure. References in this description to "an embodiment," "one embodiment," or the like, mean that a particular feature, structure, material, or characteristic being described is included in at least one embodiment of the present disclosure. Thus, the appearances of such phrases in this specification do not necessarily all refer to the same embodiment. On the other hand, such references are not necessarily mutually exclusive either. Furthermore, the particular features, structures, materials, or characteristics can be combined in any suitable manner in one or more embodiments. Also, it is to be understood that the various embodiments shown in the figures are merely illustrative representations and are not necessarily drawn to scale.

Several details describing structures or processes that are well-known and often associated with EMF detection and corresponding systems and subsystems, but that can unnecessarily obscure some significant aspects of the disclosed techniques, are not set forth in the following description for purposes of clarity. Moreover, although the following disclosure sets forth several embodiments of different aspects of the present disclosure, several other embodiments can have different configurations or different components than those described in this section. Accordingly, the introduced techniques can have other embodiments with additional elements or without several of the elements described below.

Many embodiments of the present disclosure described below can take the form of computer- or controller-executable instructions, including routines executed by a programmable computer or controller. Those skilled in the relevant art will appreciate that the introduced techniques can be practiced on computer or controller systems other than those shown and described below. The techniques introduced herein can be embodied in a special-purpose computer or data processor that is specifically programmed, configured or constructed to perform one or more of the computer-executable instructions described below. Accordingly, the terms "computer" and "controller" as generally used herein refer to any data processor and can include Internet appliances and handheld devices (including palm-top computers, wearable computers, cellular or mobile phones, multi-processor systems, processor-based or programmable consumer electronics, network computers, mini computers and the like). Information handled by these computers and controllers can be presented at any suitable display medium, including a liquid crystal display (LCD). Instructions for performing computer- or controller-executable tasks can be stored in or on any suitable computer-readable medium, including hardware, firmware or a combination of hardware and firmware. Instructions can be contained in any suitable memory device, including, for example, a flash drive, USB device, and/or other suitable medium.

The terms "coupled" and "connected," along with their derivatives, can be used herein to describe structural relationships between components. It should be understood that these terms are not intended as synonyms for each other. Rather, in particular embodiments, "connected" can be used to indicate that two or more elements are in direct contact with each other. Unless otherwise made apparent in the context, the term "coupled" can be used to indicate that two or more elements are in either direct or indirect (with other intervening elements between them) contact with each other, or that the two or more elements co-operate or interact with each other (e.g., as in a cause and effect relationship), or both.

Passive Detection Configuration

FIG. 1 is a diagram of a passive detection environment 100 for receiving EMF signals to obtain bioelectrical signals, according to some embodiments. The environment 100 can perform passive detection using an EMF sensor system to obtain bioelectrical signals such as EEG and ECG signals. The environment 100 includes a body 105 that emits EMF signals 110. The EMF signals 110 can be detected by the passive detection system 115. The passive detection system 115 includes an antenna 120 and an amplifier 125.

The antenna 120 can be a radio-frequency (RF) antenna or magnetic probe placed close to the human body. The placement may be determined by defined locations that maximize detection of EMF signals associated with various parts of the body, e.g., head, upper torso, and/or wrist. The body 105 emits EMF signals 110 that can be received by the antenna 120 of a passive detection system 115.

The received signal is then passed to amplifier 125 where the gain of the received signal is increased for further signal processing. For example, the signal detected by antenna may be amplified by a low noise amplifier (LNA). With proper frequency down-conversion, the signal can be observed and recorded for analysis.

Active Detection Configuration

Figure 2:
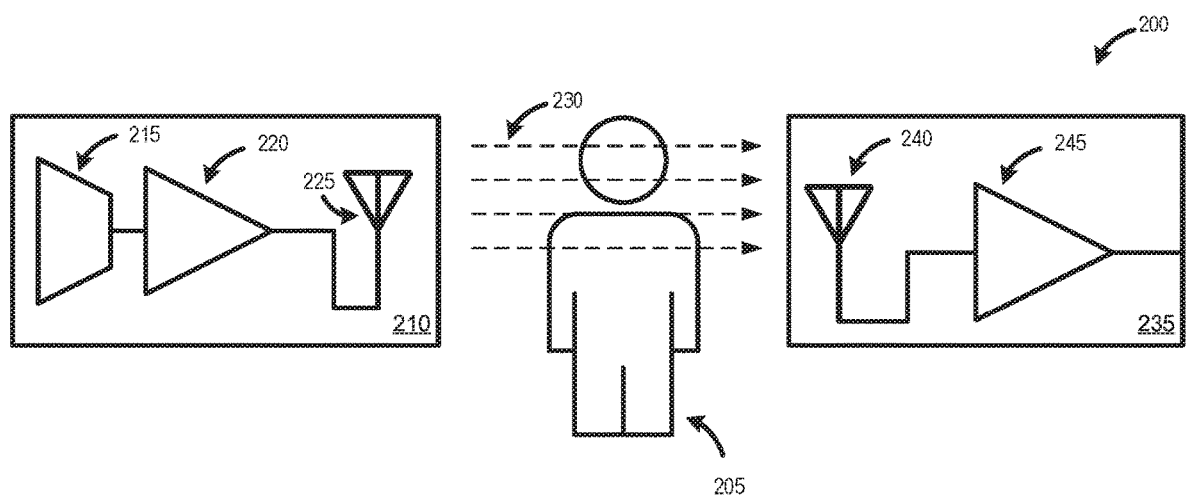
FIG. 2 is a diagram of an active detection environment in accordance with one or more embodiments of the present disclosure.

FIG. 2 is a diagram of an active detection environment 200, in accordance with some embodiments. The active detection environment 200 can utilize RF antennas to send custom or arbitrary RF waveforms and receive EMF signals from the body. Arbitrary signal generation is used to generate RF harmonic signals to propagate through the human body from RF antennas. For example, arbitrary signal generation can generate different waveforms from mathematical modeling along with different amplitudes, bandwidths, and frequencies. The environment 200 includes a human body 205, an active detection transmission module 210, and an active detection reception module 235.

The active detection transmission module 210 may be used to reflect or excite EMF signals from the human body when a wideband or narrowband external transmission source is placed near the human body. For example, a very wideband transmission may include signals from DC to 10 KHz. A narrowband transmission may be a single tone (e.g., 100 MHz). The active detection transmission module 210 includes a signal generator 215, amplifier 220, and transmission antenna 225. The signal generator 215 generates an EMF signal 230 near body 205. For example, the signal generator 215 is used to send a single tone (e.g., 100 MHz) signal to a VHF antenna.

The generated signal is amplified by amplifier 220 and transmitted using antenna 225. In some embodiments, more than one antenna may be used to transmit RF signals.

Additionally, the antennas may be placed around the human body. For example, antennas may be placed around the head, heart, chest, and abdomen. The custom magnetic and RF antennas are designed for high efficiency and compensate for body impedance at desired frequency bands.

The active detection reception module 235 receives the EMF signals transmitted by the active detection transmission module 210 and reflected or excited by body 205. The active detection reception module 235 includes antenna 240 and amplifier 245. The antenna 240 may be a radio-frequency (RF) antenna or magnetic probe placed close to the human body. The placement may be determined by defined locations that maximize detection of EMF signals associated with various parts of the body. The body 205 reflects EMF signals 230 that are received by antenna 240 of active detection reception module 235.

The received signal is then passed to amplifier 245 where the gain of the received signal is increased for further signal processing. For example, the signal detected by antenna may be amplified by a low noise amplifier (LNA). With proper frequency down-conversion, the signal can be observed and recorded for analysis Active detection using an active source enhances the weak signal signature by using a carrier signal. The transmitted carrier signal has stronger amplitude and a controlled frequency. In this setting, the introduced embodiments may use a mixer such that the human body behaves like a non-linear channel, which can generate harmonics signals when a single tone signal passes through the human body channel. The signal may be mixed with other environmental signals that enter the human body (e.g., WiFi, 4G, VHF, and/or other RF signals) or another designed test tone signal. The product of this mixing is called intermodulation (IMD) tones, which, in some cases, fall in different receive bands of the communication system.

The weak EMF signals coupled with stronger harmonic signals become new modulation signals with detectable power levels seen by a receiver. The new modulation signals include high-order intermodulated signals, including the input tones, third-order products, and high-order products. They have lower amplitudes from the carrier tones but still have a 20-dB dynamic range referring to the carrier signal amplitude level. The modulated EMF signal can be detected by the receiver and put into the demodulation process by using signal processing algorithm.

Note, however, that an active detection configuration with transmitted carrier signal may be less desirable, as compared to a passive detection configuration, in an environment where unnecessary EMF emission should be avoided (e.g., in a hostile, combative environment).

Hybrid Antenna System

Embodiments of the disclosed antenna system can detect EMF signals with different frequency ranges. Additionally, the antenna can be designed in a loop, monopole, dipole, or wire antenna placed in a certain distance from the human body. In some embodiments, the antenna may be an array or grid structure to scan the human body. In yet other embodiments, the antenna may be conformal or wearable structure embedded with textile.

The antenna system can be integrated into a body suit without inhibiting the movement of the user. The bandwidth of probe antenna and RF components are typically narrowband. Therefore, to detect and observe the whole spectrum of triggered or induced signals, very wideband components are needed. For example, very wideband components can support EMF signals from DC to 10 KHz. Contact based electrodes attach directly to the body surface. However, to use a probe antenna integrated with a textile worn by the human body, there is a gap between the sensor and the body. Therefore, non-contact antenna is provided to detect EMF signals without degradation of bio-signals.

For purposes of the present disclosure, an EMF antenna system that includes at least a contact input source (e.g., an electrode) and a non-contact input source (e.g., an antenna) may be referred to herein as a "hybrid" antenna system.

Figure 3:
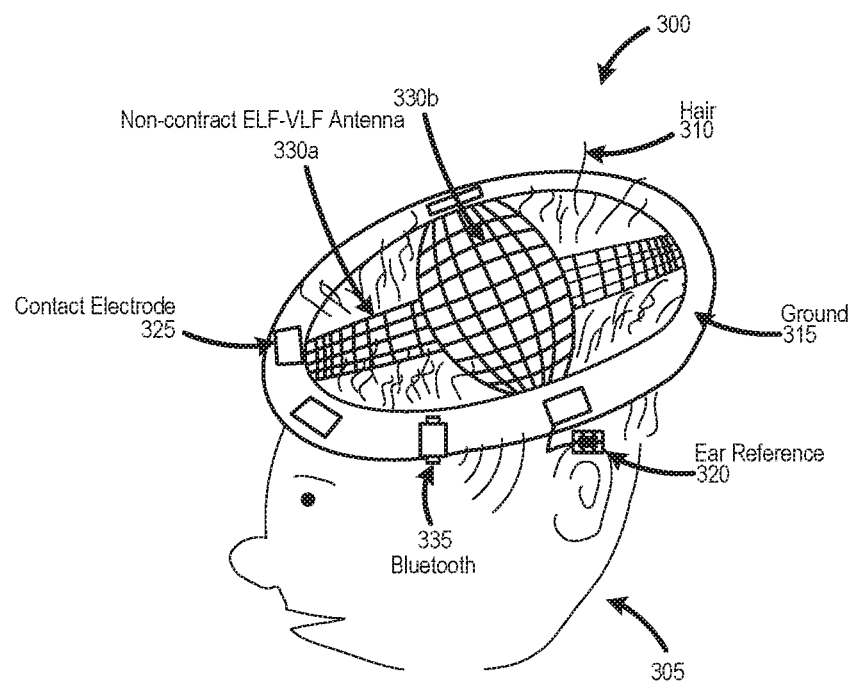
FIG. 3 depicts a diagram of an antenna system in accordance with one or more embodiments of the present disclosure.

FIG. 3 depicts a diagram of a hybrid antenna system 300 worn on the head 305 of a user to monitor the EMF signals of the user.

Hybrid antenna system 300 may use the mechanisms of EMF generation linked to the muscle electro-impulse response and energy conversations from body electrochemistry effects. The hybrid antenna system 300 uses both contact electrodes and non-contact antennas (i.e., a hybrid approach) to detect vital EMF signals. The non-contact antennas use active circuits to detect signals at such low frequencies. Hybrid antenna system 300 also detects common ground and reference signals, which are critical since they are the reference signals used to cancel the commonly seen noise (e.g., powerline noise, such as 60 Hz).

The example antenna system 300 includes a ground contact 315, an ear reference module 320, a contact electrode 325, non-contact antennas 330*a* and 330*b*, and a Bluetooth™ module 335. The entire system may be worn over the head which may include hair 310, where contact electrode placement is not suitable.

The ground contact 315 provides a return path for the signals detected by antenna system 300. The ear reference module 320 is a contact-based electrode for receiving EMF signals emitted from head 305. For example, ear reference module 320 uses traditional electrodes to connect to the skin to detect reference signals. The contact electrode 325 is also a contact-based electrode for receiving EMF signals emitted from head 305. For example, ear reference module 320 uses traditional electrodes to connect to the skin to detect EEG/ECG signals.

Many of contact-based biomonitoring electrodes of ECG and EEG are comprised of a plastic substrate covered with an Ag/AgCl compound. The electrode can be assembled with an electrolyte gel since the skin interface may contain an excess of chloride ions in solution such as perspiration. Such combination can be done by coating those compounds on the plastic substrate (i.e., stud). The gel is also used on the skin of patients when checking their ECG. However, the gel may dry out or only can last a few hours or days after placed on the patient. The conductive carbon fiber, or other conductive materials, should be qualified to replace current compound and metal materials used in current electrodes or new probes. The probe-to-skin impedance and its dimension will be decided by contact area, skin properties, and the materials used.

The electrode used in ECG detection can be a tiny patch which connects to the patient. ECG electrodes are used for sensing bioelectric potential, generally the electrical activity, caused by cardiac muscle. This electrical activity can be viewed as a small electric field or flux of charge-carrying particles (i.e., current). The electrodes work as transducers converting this current flow from the body into the electron flow of the metallic wire. After amplified and processed, the ECG signal can be observed. Very often a high ionic concentration gel is used in the skin-electrode interface to increase conductivity due to small signal magnitude. The electrode may be a silver-silver chloride electrode.

In some embodiments, the electrode module includes a plastic substrate covered with an Ag/AgCl compound, an electrolyte gel coated on the plastic substrate to provide a high ionic concentration, and a conductive material to detect EMF signals when the electrode module is in contact with a human surface. In some embodiments, an electrode module includes two pre-gel (i.e., prior to gel being applied) electrodes placed on the head of a human body to detect the vital signs of the human body.

In some embodiments, the electrode may be placed in contact with the ear to detect a reference signal. The ear is a suitable location to detect EMF signals from the body because it has relatively less noise. This is because the ear does not have any muscles and thus would not introduce EMF signals resulting from the muscle. However, other nodes can be used as needed.

The non-contact antennas 330a and 330b detect EMF signals without requiring direct contact to the human body. The non-contact antennas 330a and 330b use low frequency antennas, from extreme low frequency (ELF) to very low frequency (VLF), to collect the bioelectrical signals such as EEG/ECG signals. The antenna does not need to contact the skin directly. Thus, the antenna performs EEG/ECG signal detection at a distance from the skin that is greater than the distance between a contact-based electrode and the skin. The antenna frequency is very low (10 Hz to 10 KHz) and thus its wavelength is long (e.g., the wavelength of a 5 KHz signal is about 60,000 meters and the wavelength of a 10 Hz signal is about 30,000,000 meters). Additionally, the minimum required electrical wavelength for the traditional antenna is 0.1 wavelength to guarantee an efficient radiation efficiency.

The Bluetooth module 335 can be provided to transmit and receive data related to the signals detected by the ear reference module 320, contact electrode 325, and non-contact antennas 330a and 330b. For example, the Bluetooth module 335 may transmit the detected signals to a signal processing module for signal processing, analysis, and data storage.

The various components of the antenna system 300 can be implemented in a manner that is consistent with the various embodiments described herein.

Antenna Signal Path

Figure 4:
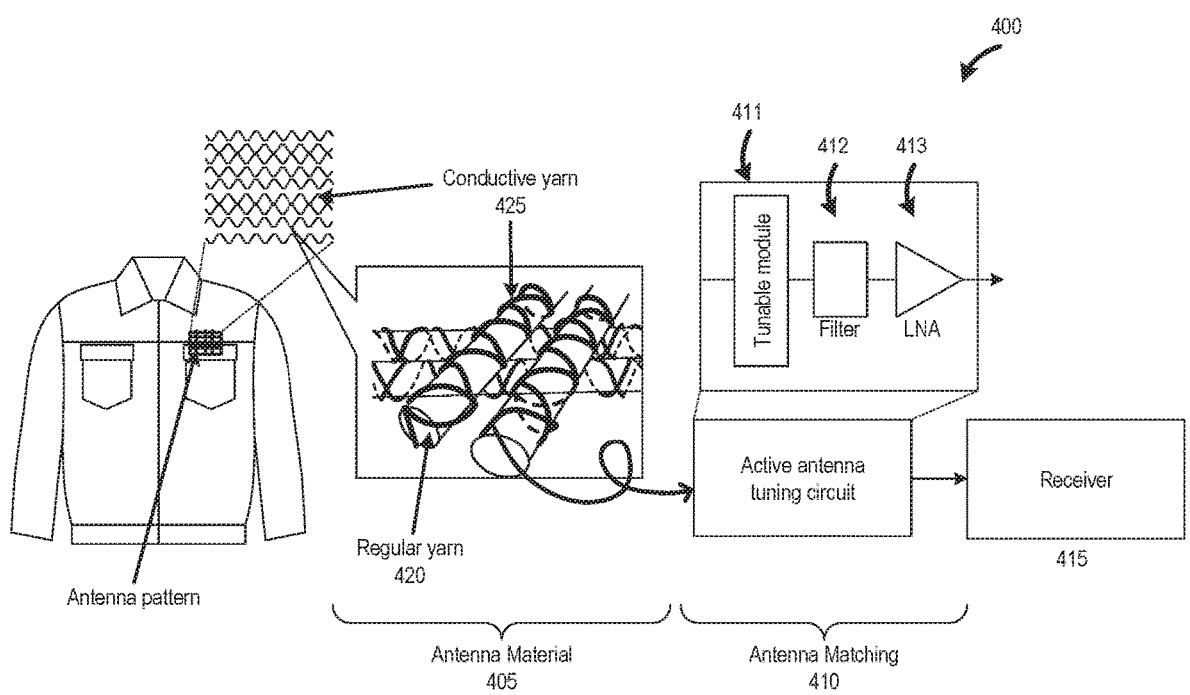
FIG. 4 depicts an antenna signal path in accordance with one or more embodiments of the present disclosure.

FIG. 4 depicts an antenna signal path 400 that includes antenna material 405, an antenna matching circuits 410, and a receiver 415. The signal path 400 represents the path of the EMF signal originating from a monitored body to an amplified for signal processing.

Antenna Material

Antenna material 405 includes a conductive material that receives EMF signals from a monitored human body. In some embodiments, the antenna is an electro-textile based antenna including non-conductive, interlacing fibers 420 and conductive yarn 425. In some embodiments, the flexible antenna patch is embedded in a flexible substrate. For example, non-conductive, interlacing fibers 420 may form a flexible antenna patch integrated into clothing worn by the monitored human body. The conductive yarn 425 may be wound around individual fibers of the non-conductive interlacing fibers 420, such that the non-conductive fiber and conductive fiber 425 form a textile patch for receiving EMF signals from a human body without contact with the human body.

Antenna material 405 may use a variety of elements or materials. In some embodiments, silver ink and copper wires are good conductors but they are less suitable to be implemented on or be part of fabric for clothing. Conductive fiber materials (e.g., electro-textile) may be used as conductive yarn so that the antenna radiator pattern can be built with the clothes in a weaving process. In some embodiments, the antenna material 405 may be a meshed antenna using conductive fiber was made by a very fine conductive silver thread (e.g., Agsis Silver AGSIS100D-1KAG).

Conductive thread is suitable since it can be used to modify existing clothing. Silver is ideal since silver oxide is highly conductive possesses excellent RF properties. Additionally, the cost of silver is significantly less than alternative conductive material such as gold.

Antenna material 405 may be used in a variety of shapes. For example, a planar antenna can be integrated with a conformal patch that fits in existing clothing. This conformal structure may cause additional resonances which may be generally undesirable. However, this property is good in this application because a wider bandwidth is desired. In some embodiments, to fit the property of the textile material, a meshed texture antenna can be used to replace the conventional patch antenna with a solid surface. Additionally, antenna material 405 may use flexible PCB materials to fabricate the meshed antenna.

In some embodiments, the antenna material 405 may be formed as a non-uniform meshed path antenna. Non-uniform meshed patch antennas have significantly less conductor coverage than a conventional meshed patch antenna. Less conductor coverage reduces the usage of the specialized conductive fiber materials, which in turn can reduce the cost of the antenna material.

Active Antenna Circuits

The antenna system uses two ways to reduce the electrical wavelength. First, the antenna system changes the transmission line materials to increase the effective electrical length. Second, the antenna system connects the shortened antenna with active antenna circuits. With the above two factors, the physical length can be greatly reduced to use a shorter antenna length to receive the vital signal from the human body. Additionally, while the environment is changing, such as when the user is in motion, the antenna system may become detuned and mismatched to the RF circuit front-end. The resulting signal loss may be significant in specific frequency ranges. Furthermore, when there is gap or other media between the body and the antenna, additional loss will result in lower signal to be received. To mitigate this impact, the active antenna circuits actively compensate for the changing conditions using the components described below.

Antenna circuits 410 includes electronic circuits that can obtain the signals received by antenna material 405 and process the signals so that they are suitable for further signal processing (e.g., at a subsequent stage, such as at the receiver module and/or the signal processing module). Antenna circuits 410 may include tunable module 411, filter 412, and amplifier 413.

Tunable module 411 facilitates wideband tuning and signal amplification. and may be implemented with tunable capacitors. Wideband tuning may facilitate reception of signals at frequencies between and including the ELF and VLF frequency bands. In some embodiments, the tunable capacitors extend the bandwidth of the antenna to include the ELF frequency band and the VLF frequency band. Filter 412 may be a band-pass or band-rejection filter that passes the input signal in most frequencies but filters signals in specific frequency bands. For example, filter 412 may pass the detected EMF signal but attenuate one or more predetermined frequencies (or frequency range(s)) for background noise suppression. Commonly seen background EMF noise can include those signals in the 60 Hz frequency band, which are typically introduced by the powerline power supply. Amplifier 413 increases the power of the signal output of filter 412. For example, amplifier 413 may amplify low frequency signals with frequencies from 5 Hz-1 KHz.

Receiver

Receiver 415 can include impedance matching modules, differential amplifiers, and filters for processing the received EMF signals from the antenna system. For example, the impedance matching module maximizes the power transfer of the received signal by matching the source load of the antenna system.

The differential amplifier enhances the gain of the received signal based upon the received reference signal. The non-contact signal and contact signal enter the instrument amplifier such as differential amplifiers. Since the amplitude from the non-contact node is amplified to a similar level of the contact node (e.g., the reference signal), the noise and interference cancellation can be performed inside the differential amplifier circuits. The filters reduce noise such as powerline noise (e.g., noise at 60 Hz).

The various components of the antenna signal path 400 can be implemented in a manner that is consistent with the various embodiments described herein.

Antenna Circuit Embodiment

Figure 5:
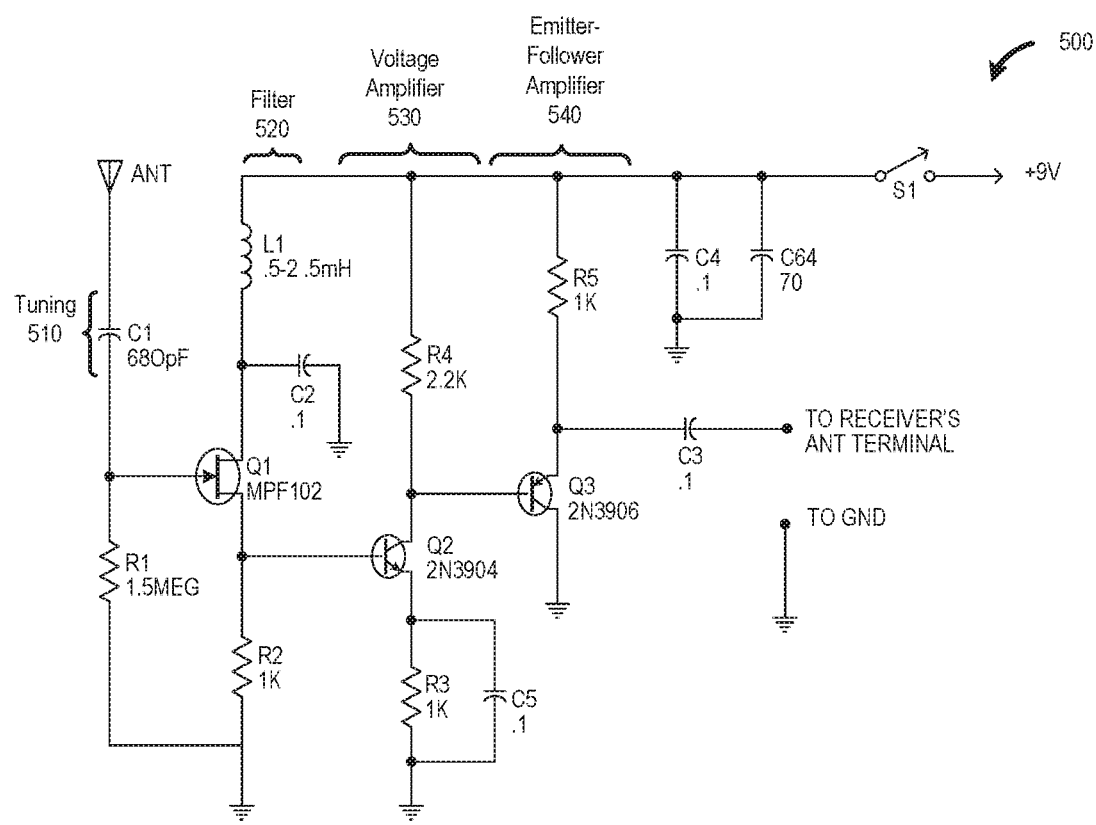
FIG. 5 depicts a circuit diagram of antenna circuit in accordance with one or more embodiments of the present disclosure.

FIG. 5 depicts a circuit diagram of antenna circuit 500 consistent with various embodiments disclosed herein. The active antenna circuit 500 includes various circuit components that may be adjusted to perform antenna matching, wideband tuning, and signal amplification. Antenna circuit 500 shown in FIG. 5 may be an embodiment of circuit 410 described above. For example, tuning circuit 510 is an embodiment of tunable module 411, filter circuit 520 is an embodiment of filter 412, and voltage amplifier 530 and emitter-follower amplifier 540 is an embodiment of amplifier 413. An active antenna circuit is distinguished from a passive antenna because the circuits utilize an external power source (e.g., DC power source 904) to power an amplifier. Additionally, the antenna circuit 500 may use bipolar junction transistors (BJT) transistors with lump elements to perform the antenna matching.

Since the body signal typically has a weak signal strength, the received signal must be amplified and filtered before the signal processing can be applied. The RF path is the first opportunity to moderate the loss and noise. For example, a high efficiency antenna and differential amplifiers may be used to maintain gain, reduce noise, and increase the chance to detect weak bioelectrical signals.

Instead of using discrete components, the antenna tuner can be a highly integrated module consisted of several switches and tunable capacitors for more flexible tuning. The bipolar junction transistor (BJT) or field emitter transistor (FET) based active circuit is used to enhance the gain and filtering. Additionally, the bandwidth of the antenna is extended while minimizing the reduction in antenna efficiency.

The various components of active antenna circuit 500 can be implemented in a manner that is consistent with the various embodiments described herein.

EMF Signal Path

Figure 6:
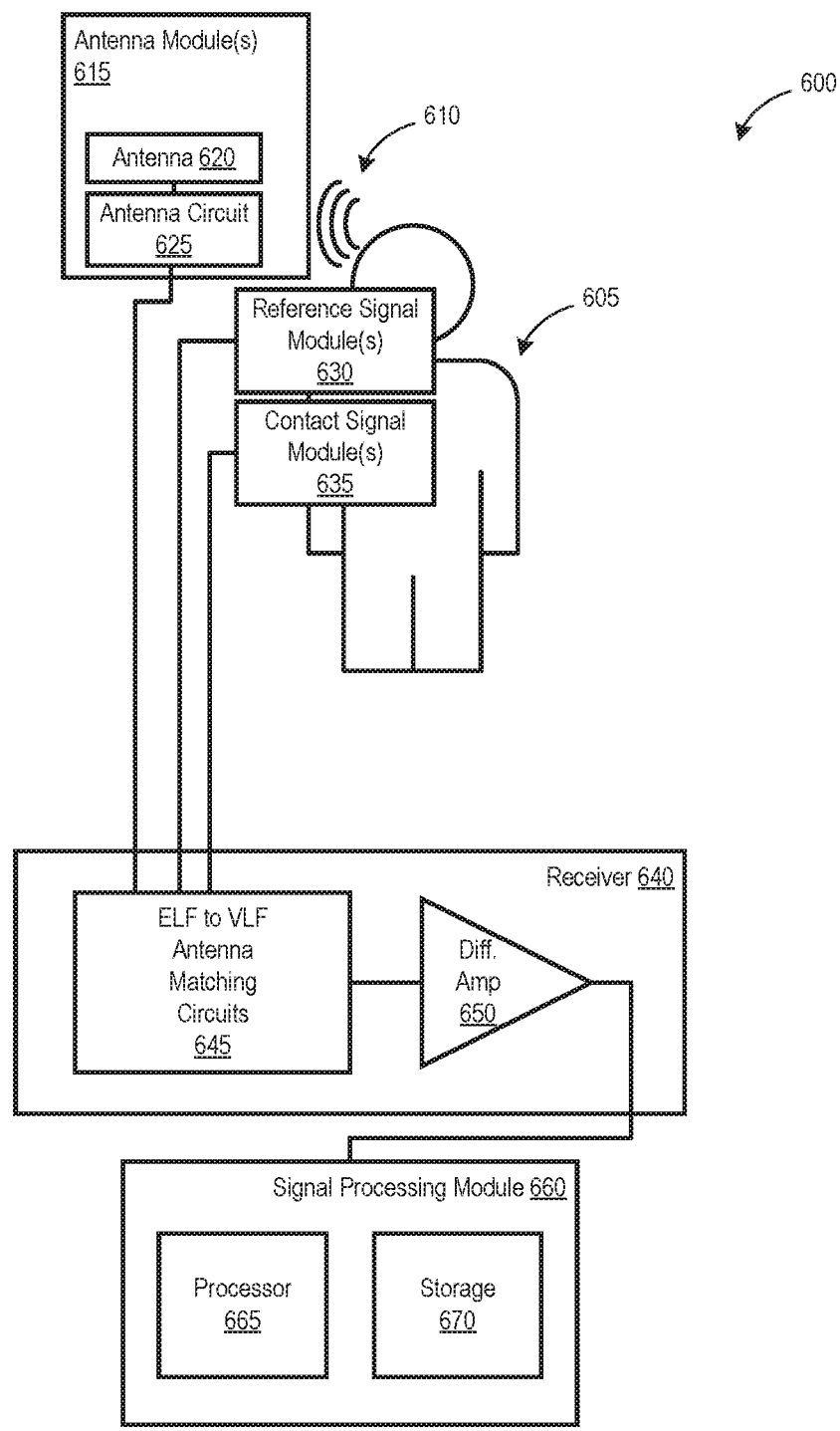
FIG. 6 depicts a block diagram of an EMF signal path in accordance with one or more embodiments of the present disclosure.

FIG. 6 depicts a block diagram of an EMF signal path 600 consistent with various embodiments disclosed herein. EMF signal path 600 is a signal path starting from the EMF signals 610 emitted from human body 605. The signals are detected by an antenna module 615, a reference signal module 630, and a contact signal module 635. The detected signals then proceed along the EMF signal path 600 to a receiver 640 and a signal processing module 650.

Antenna signal module 615 includes an antenna 620 and an antenna circuit module 625. According to one or more embodiments, the antenna 620 detects a non-contact EMF signal, and the antenna circuit module 625 performs wideband tuning and amplifies the non-contact EMF signal. For example, wideband tuning may facilitate reception of signals at frequencies between and including the ELF and VLF frequency bands.

Reference signal module 630 includes an electrode to detect a reference signal from the human body 605. For example, the electrode may be a contact-based electrode that is placed on the ear of the human body 605. The contact signal module 635 includes an electrode to detect an EMF signal from the human body 605. For example, the electrode may be a contact-based electrode placed on various parts of the human body 635 to detect localized EMF signals.

Receiver 640, in some implementations, includes an impedance matching module 645 and differential amplifier 650. Impedance matching module 645 improves the power transfer of the EMF signals by matching the source impedance of the antenna module. Differential amplifier 650 generates bioelectrical signals including a contact bioelectrical signal by amplifying the contact EMF signal and a non-contact EMF signals Signal processing module 650, in some implementations, includes processor 665 and storage 670. Processor 665 applies a filtering algorithm to improve the signal-to-noise ratio of the bioelectrical EMF signals and to perform digital signal processing on the bioelectrical EMF signals. Storage 670 provides data storage to maintain data regarding the detected EMF signals. The stored data may be used to perform further signal processing in the future. For example, signals may be stored until enough signal data is gathered to perform comparison or correlation related analysis.

The various components of the EMF signal path 600 can be implemented in a manner that is consistent with the various embodiments described herein.

EMF Detection System

Figure 7:
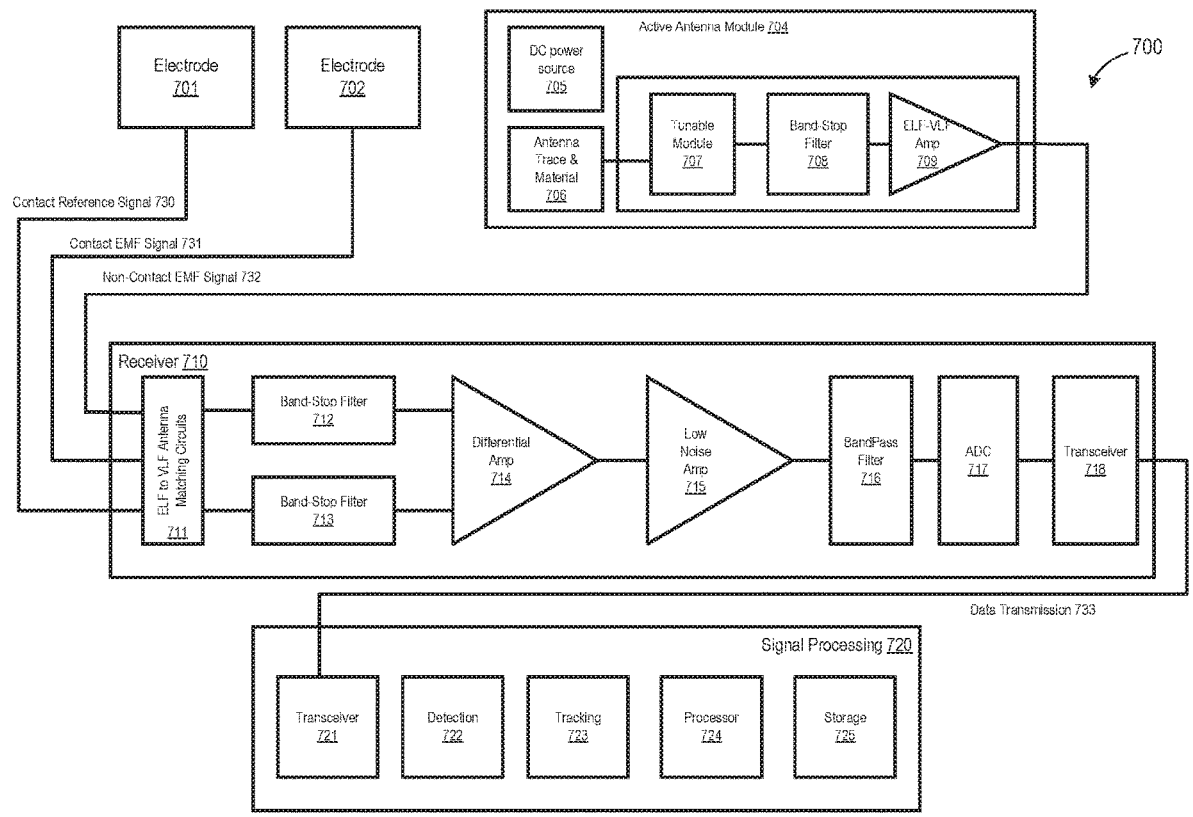
FIG. 7 depicts a block diagram of an EMF signal path in accordance with one or more embodiments of the present disclosure.

FIG. 7 depicts a block diagram of an EMF detection system 700 consistent with various embodiments disclosed herein. EMF detection system 700 includes an electrode 701, an electrode 702, an active antenna module 704, a receiver 710, and a signal processing module 720.

Electrode 701 may include a contact-based electrode to detect a reference signal 730 from a human body. In some embodiments, the electrode may be a contact-based electrode that is placed on the ear of the human body. The ear is a suitable contact point for the electrode because it does not contain muscle tissue which emits EMF signals. Thus, the detected signal includes the desired EMF signals indicating the physical condition of the monitored body and contains less noise that interferes with the desired signal. In other embodiments, electrode 701 may be placed on the neck or other locations that allow direct contact with the skin of the body. Electrode 701 outputs contact reference signal 730, which is based on the detected reference signal. For example, electrode 701 outputs reference signal 730 to receiver 710 to prepare the signal for signal processing.

Electrode 702 may include an electrode to detect an EMF signal from a human body. For example, the electrode may be a contact-based electrode that is placed on the head of the human body to measure EEG signals. The contact-based electrode is placed in direct contact with skin in order to detect the EEG signals such as on the forehead or neck. The placement of the contact-based electrode should avoid hair because hair does not conduct current and thus does not transmit EMF signals. More than one contact-based electrode may be placed on the head to collect more than one EMF signals from the human body. For example, the contact-based electrode may be placed on various parts of the head to detect localized EEG signals. This is important because EEG activity in different parts of the brain may indicate distinguishable physical conditions or brain activities. Electrode 702 outputs contact EMF signal 731. For example, electrode 702 outputs contact signal 731 to receiver 710 to prepare the signal for signal processing.

Active antenna module 704 includes direct current (DC) power source 705, antenna trace and material 706, tunable module 707, band-stop filter 708, and ELF-VLF Amplifier 709. DC power source 705 provides power to operate the antenna circuits (e.g., tunable module 707, band-stop filter 708, and ELF-VLF Amplifier 709).

Antenna trace and material 706 facilitates the detection of non-contact based EMF signals. In some embodiments, antenna trace and material 706 includes a conductive material that receives EMF signals received from a monitored human body. For example, the antenna may an electro-textile based antenna forms a flexible antenna patch. In some embodiments, the conductive yarn may be wound around individual fibers of the non-conductive interlacing fibers, such that the non-conductive fiber and conductive fiber form a textile patch for receiving EMF signals from a human body without contact with the human body. The various components of the antenna signal path 400 can be implemented in a manner that is consistent with the various embodiments described herein, such as those described at FIG. 4.

Tunable module 707 facilitates wideband tuning and signal amplification. Tunable module 707 includes tunable capacitors. In some embodiments, the tunable capacitors extend the bandwidth of the antenna to include the ELF frequency band and the VLF frequency band. Band-stop filter 708 passes the signal in most frequencies unaltered but filters signals in specific frequency bands. A band-stop filter may also be a band-rejection filter. For example, band-stop filter 708 may pass the detected EMF signal from antenna trace and material 706 but attenuates the signal in the 60 Hz frequency band. This reduces the noise introduced by the powerline power supply (e.g., DC power source 705). ELF-VLF amplifier 709 increases the power of the signal output of band-stop filter 708. For example, ELF-VLF amplifier 709 may amplify low frequency signals with frequencies from 5 Hz-1 KHz. As described above, ELF is defined by the ITU as electromagnetic radio waves with frequencies from 3 to 30 Hz. VLF is defined by the ITU as electromagnetic radio waves with frequencies from 3 kHz to 30 kHz. However, in some some cases, the frequencies can range from 0 kHz to 30 kHz. Thus, ELF-VLF amplifier 709 may amplify frequencies from 5 Hz-1 KHz in order to amplify all signals between the ELF and VLF frequency bands. Also noted above, ELF-VLF amplifier 709 is powered by DC power source 705.

In some embodiments the ELF-VLF amplifier 709 can be a single-ended amplifier. A single-ended amplifier uses a single input signal to product an output; unlike a differential amplifier which uses two inputs that are not in phase to generate an output. Alternatively, both a single-ended amplifier and a different amplifier can be used. In this case, a switch can be placed between the band-stop filter 708 and the filters.

After passing the non-contact EMF signal through antenna trace and material 706, tunable module 707, band-stop filter 708, and ELF-VLF Amplifier 709, the active antenna module 704 outputs non-contact EMF signal 732 to receiver 710 to prepare the signal for signal processing.

Receiver 710 processes the detected EMF signals to prepare the signals for signal processing. To achieve this, receiver 710 includes antenna matching module 711, band-stop filter 712, band-stop filter 713, differential amplifier 714, low noise amplifier 715, bandpass filter 716, analog-to-digital converter (ADC) 717 and transceiver 718.

Antenna matching module 711 ensures adequate power transfer from active antenna module 704. This is accomplished by matching the source load of the antenna module. In some embodiments, antenna matching module includes a resistor, inductor, and capacitor connected in series to create a resistor-inductor-capacitor (RLC) circuit network that is tuned to match the source load of the antenna module.

In some embodiments, the antenna matching module 711 takes into consideration the environmental impedance (as further described in conjunction with FIG. 8). The environmental impedance can be, for example, the impedance caused by the capacitance between an electrode (e.g., 701 or 702) and a part of the body where the electrode is placed or the air gap between the electrode the point of contact. In particular, because a capacitance can be formed between any two electrical conductors in proximity, the impedance of such a capacitor (e.g., environmental) can be matched at the antenna matching module 711. The impedance of a capacitor is based on the capacitive reactance of the capacitor.

Band-stop filter 712 takes the output of antenna matching circuit 711 corresponding to contact EMF signal 731 or non-contact EMF signal 732. Similarly, band-stop filter 713 takes the output of antenna matching circuit 711 corresponding to contact reference signal 730. For example, band-stop filter 712 and band-stop filter 713 may attenuate the signal in the 60 Hz frequency band to perform powerline noise rejection.

Differential amplifier 714 is an amplifier that amplifies the difference between two input voltages and attenuates the voltage common to the two inputs. In some embodiments, differential amplifier 714 amplifies the difference between the reference signal and non-contact EMF signal to produce a non-contact bioelectrical signal and amplify the difference between the reference signal and contact EMF signal to produce a contact bioelectrical signal. In other words, a non-contact bioelectrical signal is produced by using differential amplifier 714 to amplify the difference between the non-contact EMF signal and the reference signal. Similarly, contact bioelectrical signal is produced by using differential amplifier 714 to amplify the difference between the contact EMF signal and the reference signal. Although differential amplifier 714 is depicted as a signal amplifier, differential amplifier 714 may be implemented as multiple amplifiers. Each amplifier takes as input the reference signal and a detected EMF signal. As such, bioelectrical signals are generated by amplifying the difference between a detected EMF signal and the reference signal.

Low noise amplifier 715 amplifies a low-power signal without degrading the signal-to-noise (SNR) of the signal. In some embodiments, low noise amplifier 715 amplifies the output of differential amplifier 714. The amplified signal output is provided as input into bandpass filter 716. Bandpass filter 716 passes frequencies within a certain range but attenuates the signal outside of the range. In some embodiments, bandpass filter 716 passes frequencies between 5 Hz-10 KHz. This range allows signals from the ELF frequency band to the VLF frequency band to pass through. The signal passed from bandpass filter 716 is provided as input into analog-to-digital converter 717. The analog-to-digital converter 717 converts the detected EMF signals into a digital signal for digital signal processing at signal processing module 720. The digital signal output by analog-to-digital converter 717 is provided to transceiver 718 for transmission as data transmission signal 733 to signal processing module 720. In some embodiments, transceiver 718 may transmit data transmission signal 733 to signal processing module 720 via wireless transmissions. For example, transceiver 718 may be a Bluetooth enabled module that transmits data transmission signal 733 to signal processing module 720 via Bluetooth. In other embodiments, transceiver 718 may transmit data transmission signal 733 to signal processing module 720 using a wired transmission.

Signal processing module 720 may include transceiver 721, detection module 722, tracking module 723, processor 724, and storage module 725. Depending on the implementation, one or more modules can be added or removed to suit the purpose of a specific field application. Signal processing module 720 receives data transmission signal 733 from receiver 710. Signal processing module 720 applies digital signal processing, signal analysis, and data storage on received data transmission 733. Signal processing includes preliminary EMF detection and processing. Multiple measurements are performed with a variety of sampling rates and signal durations. Each measurement is analyzed using human EMF decomposition algorithm. In some frequency bands, the signals measured with or without a monitored human body show repeatable differences.

First, transceiver 721 facilitates the reception of data transmission 733. Data transmission 733 includes the digital signals produced by receiver 710. In particular, data transmission signal 733 may include contact and non-contact bioelectrical signals based on the contact reference signal 730, contact EMF signal 731, and non-contact EMF signal 732. Once data transmission signal 733 is received, transceiver 721 provides the data for processing and storage by detection module 722, tracking module 723, processor 724, and storage module 725.

Detection module 722 detects characteristics of the bioelectrical signals to identify physical conditions of the monitored body that correspond to the detected bioelectrical signals. For example, detection module 722 may perform peak detection, sampling rate control, and/or digital filtering on the amplified bioelectrical signals.

Additionally, detection module 722 searches the EEG signal patterns with the extreme conditions. For example, besides observing the traditional EEG spectrum from DC to 100 Hz, detection module 722 scans wideband spectrums up to several kHz. This design can cover the spectral range from DC to 10 kHz with 10000 (40 dB) voltage gain.

Tracking module 723 tracks changes in the bioelectrical signals. In particular, tracking module 723 tracks and associates signatures extracted from active and passive systems. In other words, tracking module 723 performs a correlation function on the bioelectrical signals with known bioelectrical signal sets to exclude uncertainty in the bioelectrical signals. The types of received signals are mostly non-stationary and instantaneous with non-periodic features. Since most signal processing algorithms are designed for stationary and periodic waveforms with at least some identifiable features, knowledge of the waveforms must first be acquired in order to apply the algorithms to non-stationary, non-periodic waveforms. After acquiring knowledge of the signal properties and being able to estimate the signal resolution in time or frequency domain in advance, the system is able to capture the signal. In some embodiments, tracking module 723 applies weighted decisions and loop detection to enhance the detection of bioelectrical signals corresponding to known bioelectrical signals. Additionally, tracking module 723 may apply machine learning and feedback to dynamically enhance the detection of known bioelectrical signals.

As described above, most of the EMF signals from the human body fall between two extremes (i.e., between ELF and VLF). Additionally, the EMF signals are generally non-stationary and non-periodic. To make data from the signal useful and reliable, the detected EMF signals may be tracked with tracking algorithms. Here the specially designed tracking filter is applied, which can be designed for multiple target tracking to associate the relevant EMF data in same track. It can be easier to track and update tracking along time, analyze the signal signature, and track the differences.

In some embodiments, tracking module 723 performs correlation function on the EMF signals with known EMF signals to exclude uncertainty in the bioelectrical signals. Correlation functions measures the similarity of two signals as a function of the displacement of one signal relative to another. For example, correlation may be performed suing a sliding dot product or sliding inner-product calculation. In some embodiments, the tracking module uses intermodulation techniques. The intermodulation techniques are applied by performing measurements at the range of frequencies of the signals to be detected and up the 7th order of harmonics of the signals to be detected.

Processor 724 analyzes the characteristics and changes of the bioelectrical signals. For example, processor 724 analyzes the EMF signals to detect EMF signals corresponding to physical conditions such as injury, health status, and physical activities.

Processor 724 performs human EMF mode decomposition to decompose a signal into intrinsic mode functions (IMF) along with a trend, and obtain instantaneous frequency data. It is designed to work well for data that is nonstationary and nonlinear. Empirical mode decomposition (EMD) may be used to decompose the signal into different IMFs. The IMFs which may contain possible EMF modulations can be selected into next stage for post signal processing.

Processor 724 performs signal enhancements. One effective way to enhance the signal is to apply a matched filter. A matched filter is a signal processing technique used to increase the signal to noise ratio (SNR). Usually a perfectly matched filter can increase the signal level by 50 dB. To get ideal signal enhancement, a long sequence waveform is stored in correlation memory. In some embodiments, the long sequence waveform may be stored in data storage module 725.

To characterize the EEG signals, processor 724 uses an 8 dB wavelet function to decompose the EEG signals into bandwidths known as alpha, beta, theta, delta, and gamma waves. The decomposed signals and FFT spectra may be analyzed. For example, the alpha wave, which can associate with eye closing, has a larger amplitude when the monitored body performs an eye blink compared to when the monitored body is in a relaxed state without performing an eye blink. In some embodiments, processor 724 applies a filtering algorithm to remove noise in a time-frequency domain to perform spectrogram digital signal processing on the bioelectrical signals. Processor 724 may also apply a filtering algorithm in a time domain and frequency domain to perform time domain and/or time-frequency domain digital signal processing on the bioelectrical signals.

The various components of the EMF detection system 700 can be implemented in a manner that is consistent with the various embodiments described herein.

Figure 8A:
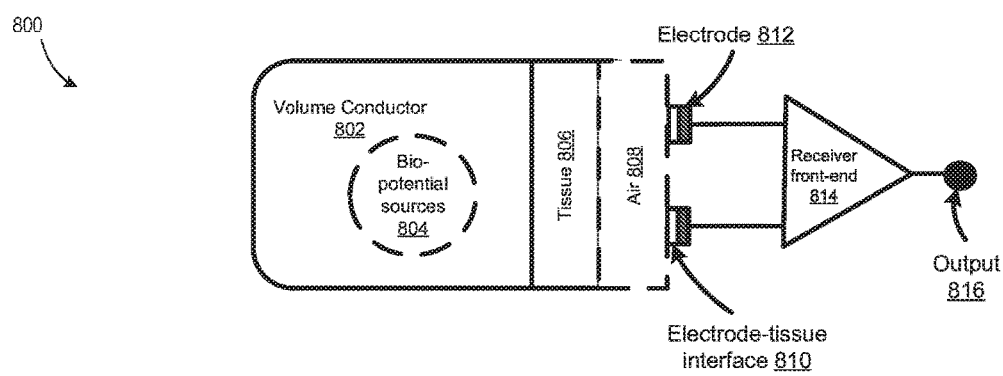
FIG. 8A depicts block diagram of an environment in which a typical EEG measurement is taken.
Figure 8B:
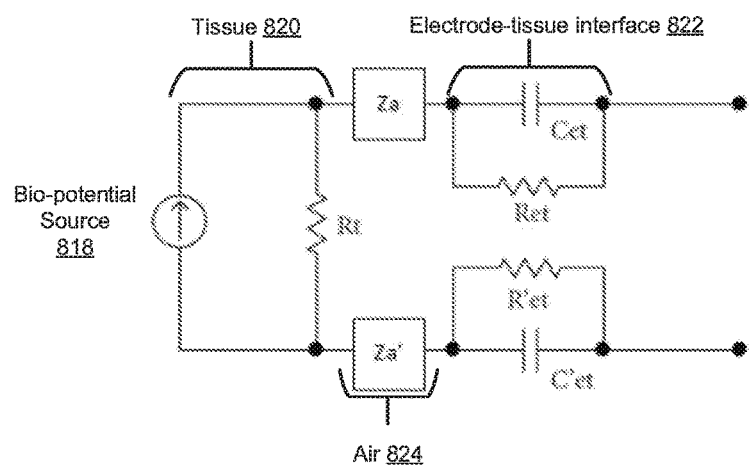
FIG. 8B depicts a circuit diagram of the environment in which a typical EEG measurement is taken.

FIG. 8A depicts block diagram of an environment 800 in which a typical EEG measurement is taken. FIG. 8B depicts a circuit diagram of the environment 800 in which a typical EEG measurement is taken. In particular, FIG. 8B depicts elements from FIG. 8A in circuit form. FIGS. 8A and 8B are described in conjunction below with reference to elements from both figures. Environment 800 includes a volume conductor 802, biopotential sources 804 and 818 (e.g., current sources), tissue 806 and 820, air 808 and 824, electrode-tissue interface 810 and 822, electrode 812, receiver front-end 814 and output 816. Traditionally, the air 808 is removed during EEG measurement. However, while removing the air 808 is possible in a controlled environment (e.g., a lab), it is less possible in the real-world. Thus, the environment 800 has to account for the impedance caused by the air 808.

For example, the electrode-tissue interface 822 can help account for the impedance caused by air 808. The $C_{et}$ and $R_{et}$, and $C'_{et}$ and $R'_{et}$ can be modified to account for $Z_a$ and $Z_a'$. In another example, the internal impedance of receiver front-end 814 can modified to match the impedance of the air 808. For instance, the resistance of tissue/skin, 820 and 806, is usually high, in the Kilo-Ohm or Mega-Ohm level. To match this impedance, the receiver front-end 814 can be designed to have a similar impedance (e.g., ELF to VLF Antenna Matching Circuits 711 in FIG. 7).

In some embodiments, the air 808 and 824, in the non-contact mode, can provide an impedance that does not match with the original matching condition and thus, causes an unbalanced voltage on the two electrodes. The unmatched impedances are then reflected in the fluctuation of the output. To address this issue, in addition to the solutions discussed above, the size and shape of the electrodes 812 can be varied so that the electric potential from each of them to the tissue 806 and 820 is different. Subsequently, the variance in the electrodes 812 can balance the capacitances of air 808 and 824 and in turn, balance the impedance of the whole system.

For example, the electrodes 812 can be placed within a helmet. The electrodes 812 (e.g., non-contact), will likely experience impedance changes due to the unstable gap between the head and the electrodes 812. Thus, the electrodes 812 can have an active gain with a wide dynamic range to compensate for the impedance differential. By doing so, the impedance caused by the electrode-tissue interface 822 and 810, can match the output impedance at the output 816 (e.g., EEG recorder).

Figure 9:
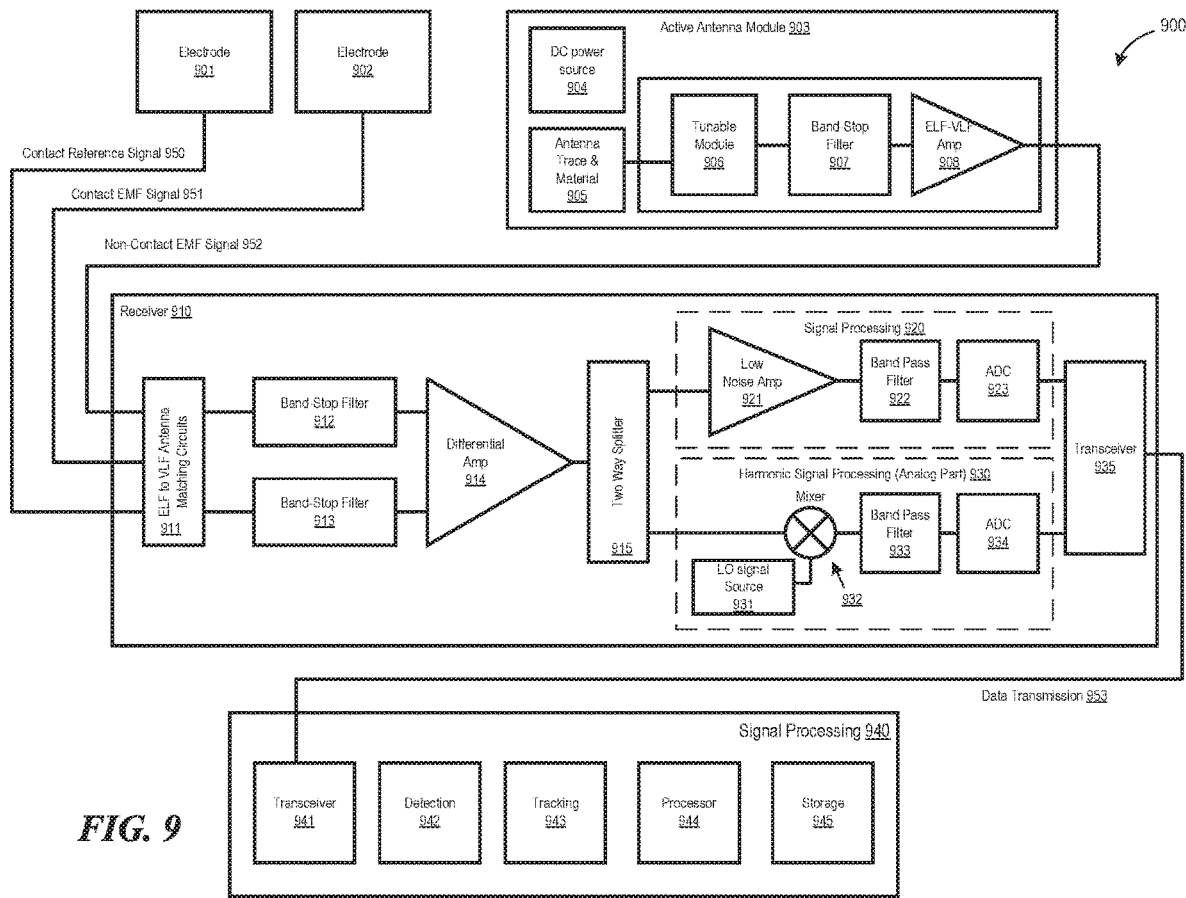
FIG. 9 depicts a block diagram of an EMF signal path in accordance with one or more embodiments of the present disclosure.

FIG. 9 depicts a block diagram of an EMF detection system 900 consistent with various embodiments disclosed herein. Many of components disclosed in EMF detection system 900 are consistent with the components disclosed in EMF detection system 700. In addition to components common to both systems, EMF detection system 900 also includes additional harmonic signal processing module 930. Harmonic signal processing is based on the concept that a signal is composed of a sum of oscillatory components.

The output of differential amplifier 914 is input into two-way splitter 915. Two-way splitter 915 then outputs the input to both signal processing module 920 and harmonic signal processing module 930. Harmonic signal processing 930 receives a signal to perform harmonic signal processing.

Harmonic signal processing 930 includes a LO signal source 931, mixer 932, band pass filter 933, and ADC 934. LO signal source 931 comprises a local oscillator that is used with mixer 932 to change the frequency of a signal. The local oscillator may be a crystal oscillator that provides stability and high performance for a fixed frequency. Alternatively, the oscillator may be a variable-frequency oscillator to provide signals at different frequencies. Together, the LO signal source 931 and mixer 932 functions as a converter that converts the frequency of the signal received from two-way splitter 915. The converted signal is then sent through band-pass filter 933 and ADC 934.

Band pass filters passes frequencies within a certain range but attenuates the signal outside of the range. In some embodiments, bandpass filter 933 passes frequencies between 0.8-10 KHz. The signal passed from bandpass filter 933 is provided as input into analog-to-digital converter 934. The analog-to-digital converter 934 converts the EMF signals into a digital signal for digital signal processing (DSP) at signal processing module 940.

Using the harmonic signal processing module 930, harmonic testing harmonic testing may be performed using: (1) signal tone sine wave, (2) frequency modulated continuous-wave (FMCW) signal with a 3-kHz bandwidth, (3) noise with a 3-kHz bandwidth, and (4) an up-converted ECG signal. Each waveform can be mixed with a 10-kHz LO signal by mixer 932. The time domain, frequency domain and the 3rd harmonics for each scenario are examined to find the signature of ECG waveform after mixing with the designated LO signal. Based upon harmonic testing, it is determined that the 3rd harmonic spectral signature of the up-converted ECG signal is like a single-tone waveform.

Harmonic signal processing can be performed in order to understand and calibrate the intermodulation from the mixer, cables, signal generators, and digitizer of the system. In one or more examples, a two-tone measurement around the frequency range of the interested signals and up to the 7th order of its harmonics is performed.

The various components of the EMF detection system 900 can be implemented in a manner that is consistent with the various embodiments described herein.

Feature Extraction and Classification

Figure 10:
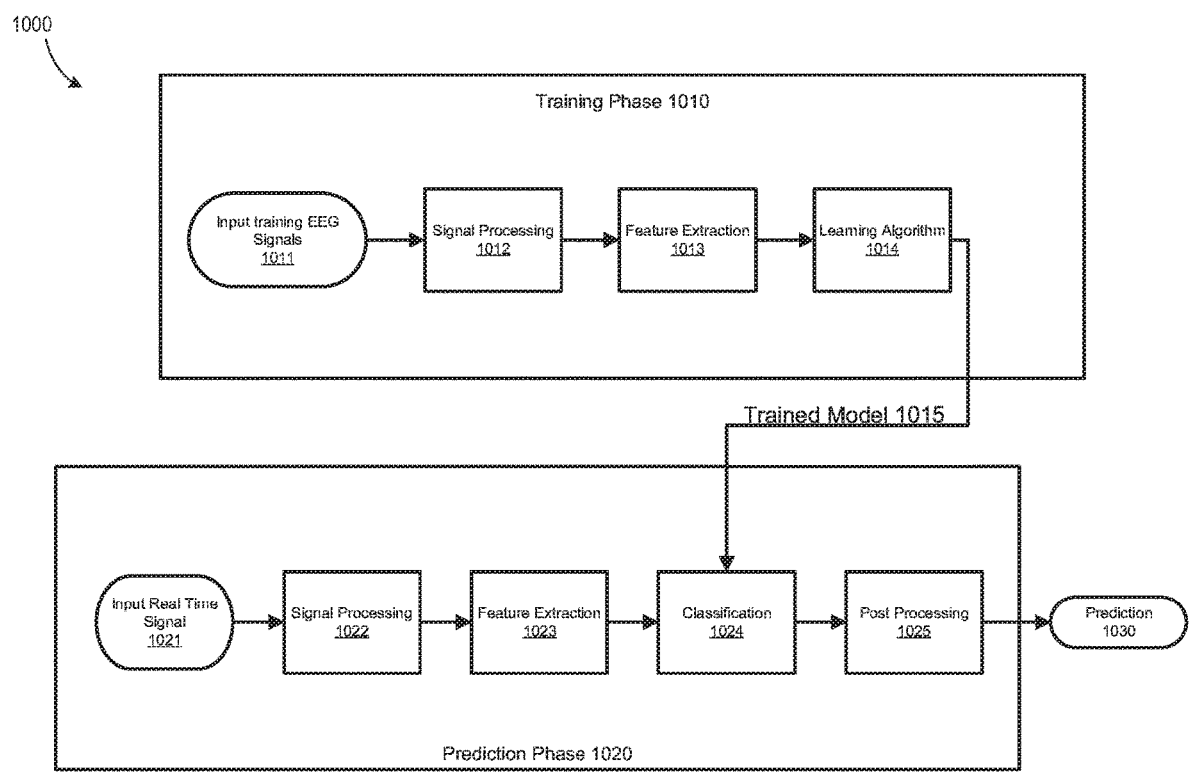
FIG. 10 depicts a diagram of a procedure of EEG feature extraction and classification.

FIG. 10 depicts a diagram of a procedure 1000 of EEG feature extraction and classification. EEG is a standard neuroimaging tool for clinicians to study brain activities and assess traumatic brain injuries. Researchers have investigated "Quantitative-EEG" (QEEG) for evaluating neural activities. Time and frequency domain features such as power spectrum, autoregressive coefficient, and frequency bands are traditionally used in such studies. Procedure 1000 is an EEG classification model based on the wavelet transform (WT), which helps identify brain activities. Procedure 1000 include two main phases: training phases 1010 and prediction phase 1020.

In the training phase 1010, training EEG signals at input at 1011. The training EEG signals are acquired in a series of controlled scenarios and can be used to create a classification model. In the prediction phase 1020, the trained model 1015 can be used to categorize or group EEG signals into different categories or groups. Feature extraction, 1013 and 1023, can be a critical step in classification. In particular, several methods of feature extraction can be used; for example, time-frequency domain analysis and discrete wavelet transform (DWT). In some embodiments, DWT can be used for EEG classification because wavelet based analysis is known to be highly effective for non-stationary EEG signals compared to short-time Fourier transformation (STFT). Similar the Fourier transform, wavelet transforms represent a signal through a linear combination of their basis functions. DWT decomposition includes successive high and low pass filtering of a time series with a down-sampling rate of, for example, two.

Once the signals are input at block 1011 and 1021, the system performs signal processing at blocks 1012 and 1022. At blocks 1012 and 1022, the EEG signals are decomposed into different sub-bands using the DWT. Subsequently, the relative wavelet energy feature can be calculated and normalized to zero mean and unit variance. The mean and variance can be optimized using Fisher's discriminant ration (FDR) and principal component analysis (PCA). The wavelet energy for each decomposition level i can be calculated as:

$$E_{D_i} = \Sigma_j |D_{ij}|^2, \ i=1,2,\ldots l \qquad (1)$$

and $$E_{A_i} = \Sigma_j |A_{ij}|^2, i=1,2,\ldots l \qquad (2)$$

So, the total energy can be defined as:

$$E_{Total} = (\Sigma E_{D_i} + E_{A_i}) \qquad (3)$$

The relative wavelet energy is calculated as:

$$E_r = \frac{E_j}{E_{Total}} \qquad (4)$$

Subsequently, the wavelet energy can be a feature extraction, at blocks 1013 and 1023. Several machine learning classifiers (e.g., algorithms) can be applied at classification block 1024 to predict the class in which a feature belongs. A classifier can asses a number of parameter, such as those received from a training model 1015. A trained classifier, as applied at learning algorithm 1014, can model the association between classes and corresponding features and is capable of identifying new instances in an unseen dataset. The following description includes a non-exhaustive description of classification methods that can be applied.

A support vector machine (SVM) is a supervised learning algorithm that uses kernels to transform input data into higher dimensional space before segregating the data via a hyper-plan with maximal margins. Generally, SVM can manage large datasets, and thus, can be used for binary classification in machine learning. Naïve Bayes (NB) classifier provides a probabilistic classification based on Bayes' theorem. The theorem posits that extracted features are not dependent. Thus, the NB model uses a maximum probability algorithm to determine that class of earlier probabilities, and a feature's probability distribution from a training dataset. The results are then employed with a maximized posterior depiction tree to find the specific class label for a new test instance. K-nearest neighbor (k-NN) is a supervised learning algorithm that identifies a testing sample's class according the majority class of k-nearest training samples.

For example, when using the wavelet energy as a feature to build the EEG classifiers in the training phase 1010, the effectiveness of the above and other classification methods can be used to obtain optimized EEG classifier for identifying brain activities and health status (e.g., at block 1014). Further, in some embodiments, a classifier can be developed by tracking the peaks of a signal and feeding the peak values and time instances to a tracking algorithm to predict future instances of the peaks. Thus, by using previous peak values and predicted future values as input into classifiers, the classifiers can be better trained.

In some embodiments, several algorithms can be applied to the accumulated historical data (e.g., previous peak values) to predict future values, such as peak values. For example, tracking algorithms can be applied to predict future values of multiple signals based on the history of each signal (e.g., contact or non-contact). The common track algorithms are nearest neighbor, probabilistic data association, multiple hypothesis tracking, and interactive multiple model.

In some embodiments, classification 1024 can include a combination of algorithms such as the linear prediction or Kalman Filter prediction. For example, the classification 1024 process can include segmenting the data into time frames with multiple data points in each segment. The data points can include three dimensions: time index, frequency, and power spectrum. Next, the tracking parameters can be established to determine which data points are includes in the segments. The data can be then transformed into the original raw data for further classification (e.g., a feedback loop process).

As such, the procedure 1000 can be implemented to detect EEG signals from a human doing normal activities. For example, a data set of EEG signals collected during walking, arm swinging, and leg moving can be used to training the model. Each EEG signal can have be 100 seconds long and partitioned (e.g., at block 1012 and/or 1022) into 5-second long segments. Each segment can be decomposed into different frequency bans (e.g., alpha beta, delta, gamma, and theta). Subsequently, at block 1013, the spectral power of each segment can be calculated using, for example, the SVM model. Using the trained model 1015, at the prediction phase 1020, another data set acquired, for example, under the same conditions, can be used to arrive at a prediction 1030.

In some embodiments, a combination of SVM models and Hilbert-Huang transform (HHT) can be used. The HHT consists of two parts: empirical model decomposition (EMD) and Hilbert spectral analysis. The decomposition is based on the assumption that any data consists of different simple intrinsic models of oscillations. Each intrinsic mode represents an oscillation. Each oscillation can be represented by an intrinsic mode function (IMF) with the following definitions: in the whole dataset, the number of extreme values and zeroes must either equal or differ by one at most; and at any point, the mean value of the envelope defined by the local maxima and the envelope defined by the local minima is zero. For example, a dataset can include EEG signals during standing and walking. The signals can be decomposed using HHT and then input into an SVM model for classification. In other words, rather than using the wavelet energy as features, the results of the HHT calculation can be used as features.

In some embodiments, a clustering process can be used application to obtain features of a signal prior to classification. This can be useful when one needs to separate the main human activity from other neuro signals. To do so, the clustering process can be based, on for example, signature distances, between EEG signals. The signature distance be from different domains (e.g., time, frequency, energy, velocity, or acceleration). For example, data can be clustered based on time. Thus, in the training phase 1010, the data from known human activity can be clustered. For instance, when a person moves an arm or a leg at certain times, the EEG signal can be at the time instance can clustered as an arm or leg movement, respectively.

In addition to clustering, the clusters can be input into an HHT to generate further categorized features. In other words, the output from one process (e.g., clustering) can be input into another process (e.g., HHT). For example, for a data set, a system can calculate the amplitude (e.g., power) distributions at each EEG band. Next, the system can calculate amplitude distributors of each band and perform clustering classification to group the EEG signals traces to similar clusters based on power. Lastly, the system can perform amplitude distributions of each cluster. The distributions can then, optionally, be fed into another model such as the HHT.

In some embodiments, the EEG signal classified using neural networks. A neural network is an artificial network which can be used for predictive modeling to derive conclusions from a seemingly unrelated dataset. A neural network breaks down the input into layers of abstraction. It can be trained using many examples to recognize patterns in speech or images, for example, just as the human brain does. Its behavior is defined by the way its individual elements are connected and by the strength, or weights, of those connections. These weights are automatically adjusted during training according to a specified learning rule until the artificial neural network performs the desired task correctly. For example, EEG signals from contact mode sensors and non-contact mode sensors can be compiled and input into a neural network. The neural network can be trained to differentiate between contact and non-contact based data.

In some embodiments, neural networks can be used to classify (e.g., decompose) both ECG and EEG signals. For example, raw ECG and EEG signals can be input into a system (e.g., a processor). The system can then take the absolute value and normalize the raw data before segmenting the raw data. In order to segment the raw data, a predetermined rule can be applied. For instance, if the raw data includes data from a fifteen minute period, the first twelve minutes can be segmented as training data, and the remaining three minutes can be segmented as test data. Each segment of data can then be input into a neural network model.

Initially, in some embodiments, the training data can be input into the neural network model to train the model. Once the training data has been parsed, the test data can be input into the neural network model. Further, training labels and test labels can be input into the neural network model so that the model can label the segmented data. Alternatively, the training data, test data, training labels, and test labels can be input into the neural network model simultaneously. In some embodiments, each input can be input in a particular order, individually, or in any other fashion. Once the data has been parsed, the neural network model can output the cost and accuracy of the training and test data.

Cost represents, for example, a mapping of data to a real number, which associates the loss of an incorrect classification. Accuracy represents, for example, the number of correct classifications amongst the total number of predictions. Thus, by assessing the loss and accuracy, the effectiveness of the neural network model can be determined. For example, in data taken over a fifteen minutes period, if cost and accuracy are poor, the system may require a solution. A solution can be, for example, increases the granularity of the data points, changing the period in which data is collected, changing the neural network model, or changing how the raw data is segmented.

Figure 11:
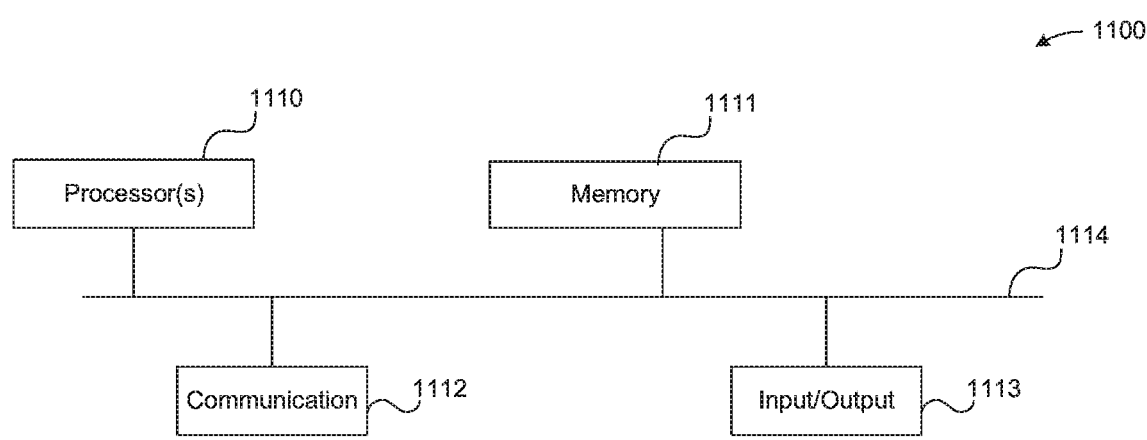
FIG. 11 is a high-level block diagram illustrating an example of a processing system in which at least some operations described herein can be implemented, consistent with various embodiments.

FIG. 11 is a high-level block diagram illustrating an example of a processing system in which at least some operations described herein can be implemented (e.g., signal processing modules 660, 720, 940), consistent with various embodiments. The processing system can be processing device 1100, which represents a system that can run any of the methods/algorithms described above. A system may include two or more processing devices such as represented in FIG. 9, which may be coupled to each other via a network or multiple networks. A network can be referred to as a communication network.

In the illustrated embodiment, the processing device 1100 includes one or more processors 1110, memory 1111, a communication device 1112, and one or more input/data (I/O) devices 1113, all coupled to each other through an interconnect 1114. The interconnect 1114 may be or include one or more conductive traces, buses, point-to-point connections, controllers, adapters and/or other conventional connection devices. Each of the processors 1110 may be or include, for example, one or more general-purpose programmable microprocessors or microprocessor cores, microcontrollers, application specific integrated circuits (ASICs), programmable gate arrays, or the like, or a combination of such devices. The processor(s) 1110 control the overall operation of the processing device 1100. Memory 1111 may be or include one or more physical storage devices, which may be in the form of random access memory (RAM), read-only memory (ROM) (which may be erasable and programmable), flash memory, miniature hard disk drive, or other suitable type of storage device, or a combination of such devices. Memory 1111 may store data and instructions that configure the processor(s) 1110 to execute operations in accordance with the techniques described above. The communication device 1112 may be or include, for example, an Ethernet adapter, cable modem, Wi-Fi adapter, cellular transceiver, Bluetooth transceiver, or the like, or a combination thereof. Depending on the specific nature and purpose of the processing device 1100, the I/O devices 1113 can include devices such as a display (which may be a touch screen display), audio speaker, keyboard, mouse or other pointing device, microphone, camera, etc.

While processes or blocks are presented in a given order, alternative embodiments may perform routines having steps, or employ systems having blocks, in a different order, and some processes or blocks may be deleted, moved, added, subdivided, combined, and/or modified to provide alternative or sub-combinations, or may be replicated (e.g., performed multiple times). Each of these processes or blocks may be implemented in a variety of different ways. In addition, while processes or blocks are at times shown as being performed in series, these processes or blocks may instead be performed in parallel, or may be performed at different times. When a process or step is "based on" a value or a computation, the process or step should be interpreted as based at least on that value or that computation.

Software or firmware to implement the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM), random access memory (RAM), magnetic disk storage media, optical storage media, flash memory devices, etc.).

Figure 12:
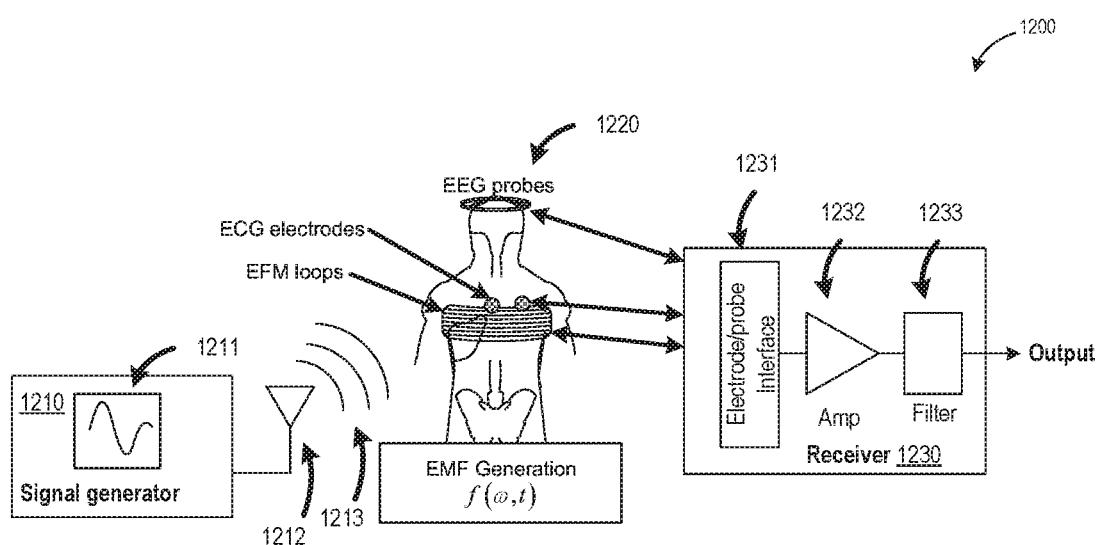
FIG. 12 is an active detection environment in accordance with one or more embodiments of the present disclosure.

FIG. 12 is an active detection environment 1200 in accordance with one or more embodiments of the present disclosure. Active detection environment 1200 includes a signal generator 1210, a monitored subject 1220, and a receiver 1230.

Signal generator 1210 includes a signal source 1211 to produce a source signal, background noise signal, and/or interference signal. The generated signal is then provided to antenna 1212 for transmission as propagated signal 1213 through monitored subject 1220. Monitored subject 1220 can be treated as a communication channel. The receiver 1230 includes an electrode/antenna interface 1221, amplifier 1232, and filter 1233. Electrode/antenna interface 1221 performs electrode/antenna matching on the electrodes and/or antennas (not shown) that detects the signals propagated across monitor subject 1220. Amplifier 1232 and filter 1233 modifies the received signal such that it is suitable for signal processing. The various components of active detection environment 1200 can be implemented in a manner that is consistent with the various embodiments described herein.

Figure 13:
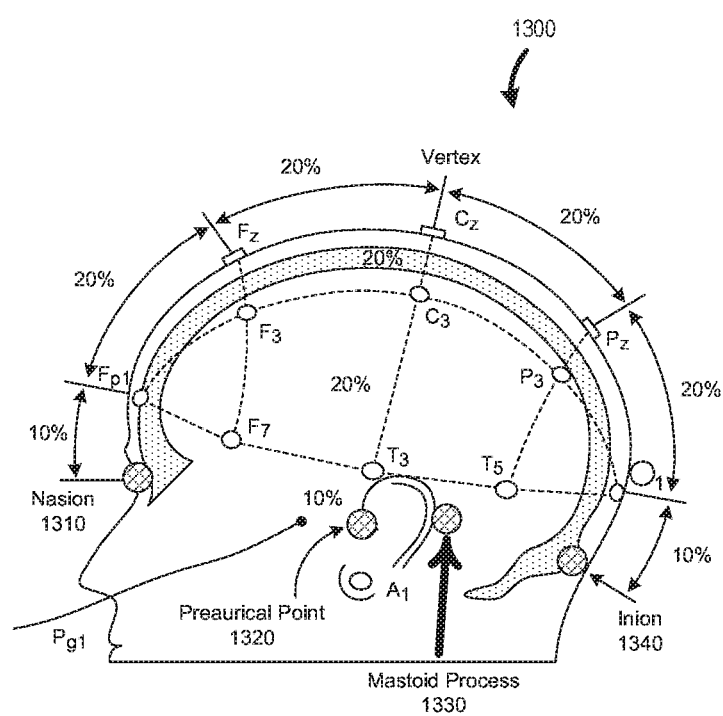
FIG. 13 depicts a chart of contact points in accordance with one or more embodiments of the present disclosure.

FIG. 13 depicts a chart of contact points where electrodes may be placed for performing contact-based EMF detection in accordance with one or more embodiments of the present disclosure. The chart shows a side-view representation of a head 1300. Contact points include the nasion 1310, preaurical point 1320, mastoid process 1330, and inion 1340. Electrodes may be used at one or more of the contact points to detect EMF and reference signals. The placement of multiple electrodes allows detection of localized EMF signals around the brain. Additionally, each contact point has different characteristics that provide different signal characteristics. For example, placement of electrodes on the ear produces less noise because there is less muscle current at that contact point. The various components disclosed in FIG. 13 can be implemented in a manner that is consistent with the various embodiments described herein.

Conclusion

From the foregoing, it will be appreciated that specific embodiments of the technology have been described herein for purposes of illustration, but that various modifications can be made without deviating from the technology. In representative embodiments, the EMF detection system can have configurations other than those specifically shown and described herein, including other circuit designs. The various modules and circuits described herein may have other configurations in other embodiments, which also produce the desired characteristics described herein.

Certain aspects of the technology described in the context of particular embodiments may be combined or eliminated in other embodiments. Further, while advantages associated with certain embodiments of the technology have been described in the context of those embodiments, other embodiments may also exhibit such advantages, and not all embodiments need necessarily exhibit such advantages to fall with within the scope of the present disclosure. Accordingly, the present disclosure and associated technology can encompass other embodiments not expressly shown or described herein. For example, while processes or blocks are presented in a given order, alternative embodiments may perform routines having steps, or employ systems having blocks, in a different order, and some processes or blocks may be deleted, moved, added, subdivided, combined, and/or modified to provide alternative or sub combinations. Each of these processes or blocks may be implemented in a variety of different ways. Also, while processes or blocks are at times shown as being performed in series, these processes or blocks may instead be performed in parallel, or may be performed at different times. Further, any specific numbers noted herein are only examples: alternative implementations may employ differing values or ranges.

To the extent any materials incorporated herein conflict with the present disclosure, the present disclosure controls.

The invention claimed is:

1. A system for detecting bioelectrical signals, the system comprising:
   a reference module having a reference electrode to detect a reference electrical signal;
   an electromagnetic field (EMF) detection module having:
      an antenna configured to detect an EMF signal;
      an antenna circuit configured to amplify the EMF signal; and
      a single-ended amplifier configured to produce a bioelectrical signal based on the amplified EMF signal;
   a receiver module having:
      an impedance matching circuit configured to match a source impedance of a prior stage; and
   a signal processing module having a processor configured to (1) perform a time-domain analysis, and/or (2) perform a discrete wavelet transform (DWT).

2. The system of claim 1, wherein the EMF detection module includes a contact electrode configured to detect a contact EMF signal while in contact with a selected area of a human body.

3. The system of claim 2, wherein the impedance matching circuit is further configured to match an impedance caused by an air gap between the contact electrode and the selected area of the human body.

4. The system of claim 1, wherein the antenna is further configured to detect EMF signals from a human body while not being in contact with the human body.

5. The system of claim 1, wherein the EMF detection module is configured to detect the EMF signal from any of a Nasion, Preaurical Point, Mastoid Process, and/or Inion located on a human head.

6. The system of claim 1, wherein the single-ended amplifier is a first single-ended amplifier located between a contact electrode and the receiver module, the system further comprising:
   a second single-ended amplifier located between a non-contact electrode and the receiver module.

7. The system of claim 1 wherein the prior stage can include one or more of the EMF detection module and/or an electrode-tissue interface.

8. The system of claim 1 wherein the processor is further configured to perform a decomposition of the detected EMF signal into electroencephalogram (EEG) bands including one or more of: alpha, beta, theta, delta, and gamma waves.

9. The system of claim 8, wherein the processor uses DWT to perform the decomposition of the detected EMF signal.

10. The system of claim 8, wherein the decomposition is performed by the processor applying one or more machine learning techniques.

11. The system of claim 10, wherein the one or more machine learning techniques include one or more of Support Vector Machine, Naïve Bayes, and/or k-Nearest Neighbor.

12. The system of claim 8, wherein the decomposition is performed by applying track algorithms, wherein the track algorithms include any of Nearest Neighbor, Probabilistic Data Association, Multiple Hypothesis Tracking, and/or Interactive Multiple Model.

13. The system of claim 8, wherein the decomposition is performed by applying a neural network model.

14. The system of claim 13, wherein the neural network model is applied to EEG and ECG signals.

15. The system of claim 8, wherein in response to performing the decomposition of the detected EMF signals, the processor is further configured to perform feature extraction on the EMF signal.

16. The system of claim 15, wherein the extracted feature is wavelet energy.

17. The system of claim 16, wherein in response to extracting the wavelet energy, the processor is further configured to normalize the wavelet to zero mean and unit variance.

18. The system of claim 15, wherein the processor is further configured to optimize the extracted features using Fisher's discriminant ration and principal component analysis.

19. The system of claim 1, wherein the processor is further configured to apply a feedback loop including a linear prediction and Kalman filter prediction.

20. The system of claim 19, wherein the processor is configured to perform the steps of (1) segmenting the EMF signal into time frames to include multiple data points; (2) determining the data dimensions of each data point; (3) establishing tracking parameters of each segment; (4) transforming the data points within each tracked segment into the original data format; and (5) inputting the transformed data points into the feedback loop.

21. The system of claim 20, wherein the data dimensions of each data point includes at least time index, frequency, and power spectrum.

22. The system of claim 1, wherein the receiver module includes a band-stop filter to reject a predetermined frequency of noise.

23. The system of claim 1, wherein the processor is further configured to enter a training phase, wherein the training phase includes (1) receiving training EEG signals; (2) performing signal processing methods on the training EEG signals; (3) extracting features from the training EEG signals; and (4) selecting a learning algorithm based on the training EEG signals.

24. The method of claim 23, wherein the processor is further configured to apply the learning algorithm while classifying the EMF signal after the EMF signal has been decomposed into EEG bands.

25. The system of claim 1, wherein the receiver module further includes a transceiver to transmit the bioelectrical signal to the signal processing module.

26. The system of claim 1, wherein the antenna is one of dipole, monopole, or loop antenna.

27. The system of claim 1, wherein the antenna is a meshed patch antenna embedded in a flexible substrate.

28. The system of claim 1, wherein the antenna is an electro-textile based antenna.

29. The system of claim 1, wherein the processor is further configured to perform time-domain analysis.

30. The system of claim 1, wherein the EMF signal has a frequency between kHz and 30 kHz.

31. The system of claim 1, wherein the processor is further configured to perform calibration based on inter-modulation and/or harmonics of the bioelectric signal.

* * * * *